United States Patent
Soejima et al.

(10) Patent No.: US 8,173,777 B2
(45) Date of Patent: May 8, 2012

(54) RECOMBINANT FACTOR X WITH NO GLYCOSYLATION AND METHOD FOR PREPARING THE SAME

(75) Inventors: Kenji Soejima, Kikuchi (JP); Takayuki Imamura, Kikuchi (JP); Ryoichi Kawamura, Kikuchi (JP); Hiroshi Nakatake, Kikuchi (JP); Arisa Maeyashiki, Kikuchi (JP); Hitomi Togo, Kikuchi (JP)

(73) Assignee: Juridical Foundation the Chemo-Sero-Therapeutic Research Institute, Kumamoto-shi (JP)

( * ) Notice: Subject to any disclaimer, the term of this patent is extended or adjusted under 35 U.S.C. 154(b) by 0 days.

(21) Appl. No.: 12/682,445

(22) PCT Filed: Oct. 8, 2008

(86) PCT No.: PCT/JP2008/068271
§ 371 (c)(1),
(2), (4) Date: Apr. 9, 2010

(87) PCT Pub. No.: WO2009/048067
PCT Pub. Date: Apr. 16, 2009

(65) Prior Publication Data
US 2010/0285568 A1    Nov. 11, 2010

(30) Foreign Application Priority Data
Oct. 9, 2007  (JP) .................. 2007-263640

(51) Int. Cl.
*C07K 16/00* (2006.01)
*C12P 21/06* (2006.01)
(52) U.S. Cl. ...................... 530/384; 435/69.1
(58) Field of Classification Search ............... 435/69.1; 530/384
See application file for complete search history.

(56) References Cited

U.S. PATENT DOCUMENTS

| | | | |
|---|---|---|---|
| 5,798,332 A | 8/1998 | Sinha et al. | |
| 2002/0068325 A1 | 6/2002 | Ng et al. | |
| 2004/0072757 A1 | 4/2004 | Wolf et al. | |
| 2009/0053185 A1 | 2/2009 | Schulte et al. | |

FOREIGN PATENT DOCUMENTS

| | | |
|---|---|---|
| EP | 1 728 798 A1 | 12/2006 |
| JP | 2005-515749 A | 6/2005 |
| WO | 2006/107084 A1 | 10/2006 |

OTHER PUBLICATIONS

M. Himmelspach, et al., "Recombinant Human Factor X: High Yield Expression and the Role of Furin in Proteolytic Maturation in Vivo and in Vitro", Thrombosis Research, vol. 97, 2000, pp. 51-67.
H. Kawashima, et al., "The effects of N-glycan of human coagulation factor X for the secretion", Biochemistry, Nov. 11, 2007, 4P-0192.
K. Hansson et al., "Post-translational modifications in proteins involved in blood coagulation", Journal of Thrombosis and Haemostasis, vol. 3, 2005, pp. 2633-2648.
Extended European Search Report issued Feb. 28, 2011, in European Patent Application No. 08837781.7.
Hiroaki Nakagawa, et al.,"Identification of the Oligosaccharide Structures of human coagulation factor X activation peptide at each glycosylation site", Glycoconjugate Journal, vol. 12, No. 2, XP-002614888, Apr. 1995, pp. 173-181.
K. Hansson et al., "Post-translational modifications in proteins involved in blood coagulation", Journal of Thrombosis and Haemostasis, 2005, 3: 2633-2648, Conf Retrovir Oppor Infect 5th 1998 Chic, 1998.
Mellquist J. et al., "Partial glycosylation at Asn-X-Ser/Thr sequons contributes to structural diversity in the V(3) region of HIV-1 gp120", NLM Gateway, (abstract).
Mellquist JL. et al. "The amino acid following an asn-X-Ser/Thr, sequon is an important determinant of N-linked core glycosylation efficiency", PubMed, Biochemistry, May 12, 1998;37(19):6833-7, abstract.

*Primary Examiner* — Tekchand Saidha
(74) *Attorney, Agent, or Firm* — Oblon, Spivak, McClelland, Maier & Neustadt, L.L.P.

(57) ABSTRACT

A Factor X (hereinafter referred to as "FX") with a high activity is provided. The present invention relates to a method for efficiently preparing a recombinant, two-chain FX which comprises intervening glycosylation at such an amino acid sequence that is essential for glycosylation in FX to thereby allow for expression of a recombinant FX with no glycosylation, and the recombinant FX with no glycosylation obtained by said method.

18 Claims, 1 Drawing Sheet

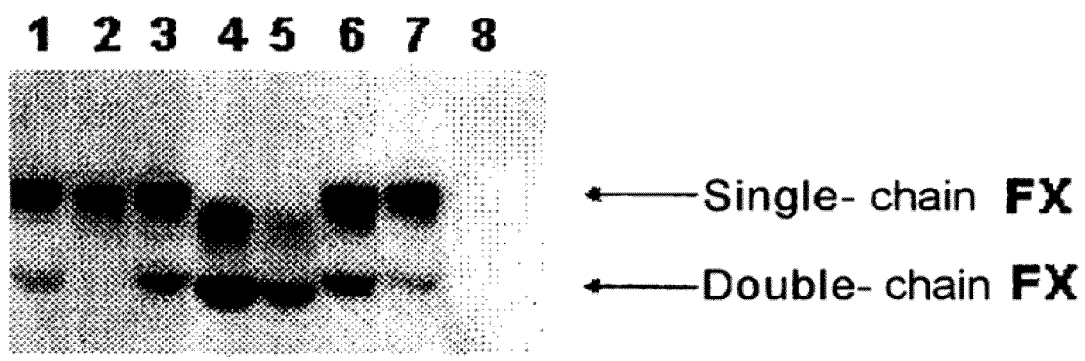

SEQUENCE LISTING

<160> NUMBER OF SEQ ID NOS: 17

<210> SEQ ID NO 1
<211> LENGTH: 448
<212> TYPE: PRT
<213> ORGANISM: Homo sapiens

<400> SEQUENCE: 1

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365
```

-continued

```
Thr Lys Gln Glu Asp Ala Cys Gln Gly Asp Ser Gly Pro His Val
    370                 375                 380
Thr Arg Phe Lys Asp Thr Tyr Phe Val Thr Gly Ile Val Ser Trp Gly
385                 390                 395                 400
Glu Gly Cys Ala Arg Lys Gly Lys Tyr Gly Ile Tyr Thr Lys Val Thr
                405                 410                 415
Ala Phe Leu Lys Trp Ile Asp Arg Ser Met Lys Thr Arg Gly Leu Pro
            420                 425                 430
Lys Ala Lys Ser His Ala Pro Glu Val Ile Thr Ser Ser Pro Leu Lys
        435                 440                 445
```

<210> SEQ ID NO 2
<211> LENGTH: 488
<212> TYPE: PRT
<213> ORGANISM: Homo sapiens

<400> SEQUENCE: 2

```
Met Gly Arg Pro Leu His Leu Val Leu Leu Ser Ala Ser Leu Ala Gly
1               5                   10                  15
Leu Leu Leu Leu Gly Glu Ser Leu Phe Ile Arg Arg Glu Gln Ala Asn
                20                  25                  30
Asn Ile Leu Ala Arg Val Thr Arg Ala Asn Ser Phe Leu Glu Glu Met
            35                  40                  45
Lys Lys Gly His Leu Glu Arg Glu Cys Met Glu Glu Thr Cys Ser Tyr
        50                  55                  60
Glu Glu Ala Arg Glu Val Phe Glu Asp Ser Asp Lys Thr Asn Glu Phe
65                  70                  75                  80
Trp Asn Lys Tyr Lys Asp Gly Asp Gln Cys Glu Thr Ser Pro Cys Gln
                85                  90                  95
Asn Gln Gly Lys Cys Lys Asp Gly Leu Gly Glu Tyr Thr Cys Thr Cys
            100                 105                 110
Leu Glu Gly Phe Glu Gly Lys Asn Cys Glu Leu Phe Thr Arg Lys Leu
        115                 120                 125
Cys Ser Leu Asp Asn Gly Asp Cys Asp Gln Phe Cys His Glu Glu Gln
    130                 135                 140
Asn Ser Val Val Cys Ser Cys Ala Arg Gly Tyr Thr Leu Ala Asp Asn
145                 150                 155                 160
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Ser Ser Gly
            180                 185                 190
Glu Ala Pro Asp Ser Ile Thr Trp Lys Pro Tyr Asp Ala Ala Asp Leu
        195                 200                 205
Asp Pro Thr Glu Asn Pro Phe Asp Leu Leu Asp Phe Asn Gln Thr Gln
    210                 215                 220
Pro Glu Arg Gly Asp Asn Asn Leu Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
        275                 280                 285
Gly Asp Arg Asn Thr Glu Gln Glu Glu Gly Gly Glu Ala Val His Glu
    290                 295                 300
```

```
Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
            325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
            355                 360                 365

Glu Lys Gly Arg Gln Ser Thr Arg Leu Lys Met Leu Glu Val Pro Tyr
            370                 375                 380

Val Asp Arg Asn Ser Cys Lys Leu Ser Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480

Val Ile Thr Ser Ser Pro Leu Lys
            485

<210> SEQ ID NO 3
<211> LENGTH: 1467
<212> TYPE: DNA
<213> ORGANISM: Homo sapiens

<400> SEQUENCE: 3
atggggcgcc cactgcacct cgtcctgctc agtgcctccc tggctggcct cctgctgctc      60
ggggaaagtc tgttcatccg cagggagcag gccaacaaca tcctggcgag ggtcacgagg     120
gccaattcct ttcttgaaga gatgaagaaa ggacacctcg aaagagagtg catggaagag     180
acctgctcat acgaagaggc ccgcgaggtc tttgaggaca cgacaagac gaatgaattc      240 tggaataaat acaaagatgg cgaccagtgt gagaccagtc cttgccagaa ccagggcaaa     300
tgtaaagacg gcctcgggga atacacctgc acctgtttag aaggattcga aggcaaaaac     360
tgtgaattat tcacacggaa gctctgcagc ctggacaacg gggactgtga ccagttctgc     420
cacgaggaac agaactctgt ggtgtgctcc tgcgcccgcg gtacaccct ggctgacaac      480 ggcaaggcct gcattcccac agggccctac ccctgtggga acagaccct ggaacgcagg      540 aagaggtcag tggcccaggc caccagcagc agcggggagg cccctgacag catcacatgg     600
aagccatatg atgcagccga cctggacccc accgagaacc ccttcgacct gcttgacttc     660
aaccagacgc agcctgagag gggcgacaac aacctcacca ggatcgtggg aggccaggaa     720
tgcaaggacg gggagtgtcc ctggcaggcc ctgctcatca tgaggaaaa cgagggtttc     780 tgtggtggaa ctattctgag cgagttctac atcctaacgg cagcccactg tctctaccaa     840
gccaagagat tcaaggtgag ggtaggggac cggaacacgg agcaggagga gggcggtgag     900
gcggtgcacg aggtggaggt ggtcatcaag cacaaccggt tcacaaagga gacctatgac     960
ttcgacatcg ccgtgctccg gctcaagacc cccatcacct tccgcatgaa cgtggcgcct    1020
gcctgcctcc ccgagcgtga ctgggccgag tccacgctga tgacgcagaa gacggggatt    1080
```

-continued

```
gtgagcggct tcgggcgcac ccacgagaag ggccggcagt ccaccaggct caagatgctg      1140
gaggtgccct acgtggaccg caacagctgc aagctgtcca gcagcttcat catcacccag      1200
aacatgttct gtgccggcta cgacaccaag caggaggatg cctgccaggg ggacagcggg      1260
ggcccgcacg tcacccgctt caaggacacc tacttcgtga caggcatcgt cagctgggga      1320
gagggctgtg cccgtaaggg gaagtacggg atctacacca aggtcaccgc cttcctcaag      1380
tggatcgaca ggtccatgaa aaccaggggc ttgcccaagg ccaagagcca tgccccggag      1440
gtcataacgt cctctccatt aaagtga                                         1467
```

<210> SEQ ID NO 4
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Ala Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285
```

-continued

```
Lys Thr Pro Ile Thr Phe Arg Met Asn Val Ala Pro Ala Cys Leu Pro
            290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

<210> SEQ ID NO 5
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Ala Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205
```

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
            245                 250                 255

Glu Gly Gly Glu Ala Val His Glu Val Glu Val Val Ile Lys His Asn
        260                 265                 270

Arg Phe Thr Lys Glu Thr Tyr Asp Phe Asp Ile Ala Val Leu Arg Leu
    275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
            325                 330                 335

Leu Lys Met Leu Glu Val Pro Tyr Val Asp Arg Asn Ser Cys Lys Leu
        340                 345                 350

Ser Ser Ser Phe Ile Ile Thr Gln Asn Met Phe Cys Ala Gly Tyr Asp
    355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
            405                 410                 415

Ala Phe Leu Lys Trp Ile Asp Arg Ser Met Lys Thr Arg Gly Leu Pro
        420                 425                 430

Lys Ala Lys Ser His Ala Pro Glu Val Ile Thr Ser Ser Pro Leu Lys
    435                 440                 445

<210> SEQ ID NO 6
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
            85                  90                  95

Asp Gln Phe Cys His Glu Glu Gln Asn Ser Val Val Cys Ser Cys Ala
        100                 105                 110

Arg Gly Tyr Thr Leu Ala Asp Asn Gly Lys Ala Cys Ile Pro Thr Gly
    115                 120                 125

```
Pro Tyr Pro Cys Gly Lys Gln Thr Leu Glu Arg Arg Lys Arg Ser Val
        130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Ala Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445

<210> SEQ ID NO 7
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
                20                  25                  30

Asp Ser Asp Lys Thr Asn Glu Phe Trp Asn Lys Tyr Lys Asp Gly Asp
            35                  40                  45
```

```
Gln Cys Glu Thr Ser Pro Cys Gln Asn Gln Gly Lys Cys Lys Asp Gly
 50                  55                  60

Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Glu Gln Asn Ser Val Val Cys Ser Cys Ala
                100                 105                 110

Arg Gly Tyr Thr Leu Ala Asp Asn Gly Lys Ala Cys Ile Pro Thr Gly
                115                 120                 125

Pro Tyr Pro Cys Gly Lys Gln Thr Leu Glu Arg Arg Lys Arg Ser Val
130                 135                 140

Ala Gln Ala Thr Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Ala Gln Thr Gln Pro Glu Arg Gly Asp Asn Asn Leu
                180                 185                 190

Thr Arg Ile Val Gly Gly Gln Glu Cys Lys Asp Gly Glu Cys Pro Trp
            195                 200                 205

Gln Ala Leu Leu Ile Asn Glu Glu Asn Glu Gly Phe Cys Gly Gly Thr
210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
                260                 265                 270

Arg Phe Thr Lys Glu Thr Tyr Asp Phe Asp Ile Ala Val Leu Arg Leu
            275                 280                 285

Lys Thr Pro Ile Thr Phe Arg Met Asn Val Ala Pro Ala Cys Leu Pro
290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
                340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
                420                 425                 430

Lys Ala Lys Ser His Ala Pro Glu Val Ile Thr Ser Ser Pro Leu Lys
                435                 440                 445

<210> SEQ ID NO 8
<211> LENGTH: 448
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 8

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Ala Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400
```

```
Glu Gly Cys Ala Arg Lys Gly Lys Tyr Gly Ile Tyr Thr Lys Val Thr
            405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

<210> SEQ ID NO 9
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320
```

```
Val Ser Gly Phe Gly Arg Thr His Glu Lys Gly Arg Gln Ser Thr Arg
            325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
        370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Ala Ser Ser Pro Leu Lys
        435                 440                 445
```

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcgtcgacc caccatggat ggggcgccca ctgcacctc                          39

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctcgagttat cactttaatg gagagga                                       27

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaatgtaaag ccggcctcgg g                                             21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gacagcatcg catggaagcc a                                             21

<210> SEQ ID NO 14
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctggaccccg ccgagaaccc c                                          21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cttgacttcg cccagacgca g                                          21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcgacaacg ccctcaccag g                                          21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaggtcatag cgtcctctcc a                                          21
```

RECOMBINANT FACTOR X WITH NO GLYCOSYLATION AND METHOD FOR PREPARING THE SAME

CROSS-REFERENCE TO RELATED APPLICATIONS

The present application is a 35 U.S.C. §371 National Stage patent application of International patent application PCT/JP2008/068271, filed on Oct. 8, 2008, which claims priority to Japanese patent application JP 2007-263640, filed on Oct. 9, 2007.

TECHNICAL FIELD

The present invention relates to a recombinant Factor X (hereinafter also referred to as "FX") that may be expressed as a two-chain protein where a high enzymatic activity and an efficient recombinant expression are possible. Specifically, the present invention relates to a method for efficiently preparing a two-chain, recombinant FX by intervening glycosylation at such an amino acid sequence that is essential for glycosylation, said amino acid sequence being present within an activation peptide domain of FX, to allow for expression of a recombinant FX with no glycosylation for improving expression efficiency.

BACKGROUND ART

It is widely known that FX is a vitamin K dependent blood coagulation factor. Like the other vitamin K dependent factors, FX possesses a Gla domain consisting of 11 γ-carboxyglutamic acids (hereinafter also referred to as "Gla") in the amino acid sequence beginning from the N-terminal to the 39th residue (Non-patent reference 1). In vitro, FX is converted into activated Factor X (hereinafter also referred to as "FXa") by an activated Factor VII (hereinafter also referred to as "FVIIa") or an activated Factor IX (hereinafter also referred to as "FIXa"). FX is used for the treatment of hemophilia patients with inhibitor where an inhibitor to FVIII or FIX is produced as a consequence of substitution therapy with said FVIII or FIX.

Human FX, in the course of its biosynthesis, is subject to posttranslational modification such as generation of Gla, cleavage of a prepro sequence (the sequence of FX after this cleavage is shown in SEQ ID NO: 1), β-hydroxylation of aspartic acid at position 63 in SEQ ID NO: 1, asparagine-type glycosylation at positions 181 and 191, serine/threonine-type glycosylation at positions 159, 171 and 443, and the like. It is thought that FX, after being synthesized as a single-chain protein, is subject to limited degradation with furin, a signal peptidase, at the cleavage motif Arg-Arg-Lys-Arg at positions 139 to 142 in SEQ ID NO: 1 to thereby secrete a two-chain protein.

For expression of a recombinant FX, the expression as a two-chain protein is the most important. It is known that a recombinant expression from an expression vector to which cDNA (SEQ ID NO: 3) encoding the amino acid sequence of FX (the amino acid sequence of FX including the prepro sequence is shown in SEQ ID NO: 2) is simply ligated results in expressed products, most of which are secreted into culture supernatant as a single-chain protein and which have a low specific activity.

In general, in recombinant factors, their expression level is often the matter. For genetic recombination of Factor X in the present invention, in addition to its expression level, the process for generating a two-chain protein was thought to be a rate-determining (Non-patent reference 2). In Non-patent reference 2, Himmelspach et al. co-expressed FX with furin so as to promote generation of a two-chain protein with as high an expression level of FX as 120 µg/ml or more but with a low activity of 25%.

Non-patent reference 1: Journal of Thrombosis and Haemostasis, 3: 2633-2648 (2005)
Non-patent reference 2: Thrombosis Research 97: 51-67 (2000)

DISCLOSURE OF THE INVENTION

Technical Problem to be Solved by the Invention

A problem to be solved by the present invention is to prepare and provide a recombinant, two-chain FX with a high activity.

Means for Solving the Problems

Under the circumstances, the present inventors have assiduously investigated so as to prepare a recombinant, two-chain FX with a high activity, and as a result, having regard to a sugar chain of FX, have succeeded in preparing a secreted, two-chain FX by intervening glycosylation, to thereby complete the present invention.

Thus, the present invention includes the following (1) to (13):
(1) A method for efficiently preparing a recombinant, two-chain Factor X (hereinafter also referred to as "FX") which comprises intervening glycosylation at such an amino acid sequence that is essential for glycosylation in FX to thereby allow for expression of a recombinant FX with no glycosylation.
(2) The method of (1) above wherein the recombinant FX with no glycosylation is a recombinant FX with no glycosylation at asparagine at position 181 (Asn181) and/or asparagine at position 191 (Asn191) in SEQ ID NO: 1.
(3) The method of (2) above wherein the recombinant FX with no glycosylation at Asn181 and/or Asn191 is obtained by substituting Asn181 and/or Asn191 with a protein-constituting amino acid other than Asn.
(4) The method of (2) above wherein the recombinant FX with no glycosylation at Asn181 and/or Asn191 is obtained by substituting threonine at position 183 (Thr183) and/or threonine at position 193 (Thr193) with a protein-constituting amino acid other than threonine (Thr) or serine (Ser).
(5) The method of (1) above wherein intervening glycosylation at such an amino acid sequence that is essential for glycosylation in FX is carried out by adding an inhibitor to glycosyltransferase during cell culture.
(6) The method of (5) above wherein the inhibitor to glycosyltransferase is tunicamycin, RNAi, or an antisense DNA.
(7) The method of (1) above wherein intervening glycosylation at such an amino acid sequence that is essential for glycosylation in FX is carried out by using a glycosyltransferase-deficient cell strain as a host cell.
(8) A recombinant FX with no glycosylation obtained by the method of any of (1) to (7) above.
(9) A gene fragment comprising a nucleotide sequence encoding the recombinant FX with no glycosylation of (8) above.
(10) An expression vector comprising the gene fragment of (9) above.
(11) A transformed cell in which the expression vector of (10) above is introduced.

(12) A pharmaceutical composition comprising the recombinant FX with no glycosylation of (8) above as an active ingredient.
(13) A therapeutic agent effective for the treatment of a hemophilia patient comprising the pharmaceutical composition of (12) above.

More Efficacious Effects than Prior Art

The recombinant FX with no glycosylation obtained in accordance with the present invention may efficiently be expressed as a two-chain protein. Accordingly, the recombinant FX of the present invention may be used as a medicament quite useful for substitution therapy to hemophilia patients, in particular, those patients possessing an inhibitor.

BRIEF DESCRIPTION OF DRAWINGS

FIG. 1 shows results of Western blot with antibodies to various recombinant FXs obtained by the present invention, showing expression patterns of the recombinant FXs in culture supernatant with BHK cells as a host. Lane 1: Variant supernatant (D63A) where aspartic acid at position 63 is substituted with alanine; Lane 2: Variant supernatant (T159A) where threonine at position 159 is substituted with alanine; Lane 3: Variant supernatant (T171A) where threonine at position 171 is substituted with alanine; Lane 4: Variant supernatant (N181A) where asparagine at position 181 is substituted with alanine; Lane 5: Variant supernatant (N191A) where asparagine at position 191 is substituted with alanine; Lane 6: Variant supernatant (T443A) where threonine at position 443 is substituted with alanine; Lane 7: Wild-type recombinant FX supernatant; and Lane 8: Negative control supernatant.

BEST MODE FOR CARRYING OUT THE INVENTION

The present inventors have focused on sites of posttranslational modification such as glycosylation and carried out amino acid substitution in FX to successfully prepare a recombinant FX having a high enzymatic activity. The recombinant FX according to the present invention is explained in detail hereinbelow.

In general, asparagine-type glycosylation is initiated at the site: Asn-X-Thr/Ser where X is any amino acid other than Pro by various glycosyltransferases in the endoplasmic reticulum followed by further modification in the Golgi body (Molecular Biology of The Cell 2nd edition, Chapter 8, Bruce Alberts et al. Garland Publishing, Inc.). Accordingly, the Asn or Thr/Ser may be substituted with other amino acids for intervening glycosylation to allow for efficient generation of a two-chain, recombinant FX and expression of the recombinant FX having a high activity.

For an amino acid to be used the purpose of amino acid substitution, alanine (Ala) is selected herein by way of example but any amino acid may be used insofar as it does not cause any significant disturbance such as loss of an enzymatic activity.

The variant with glycosylation being intervened may be obtained by using genetic recombination technique. A host cell is preferably a eukaryote such as animal cells. The variant of the present invention may be obtained by incorporating cDNA encoding an amino acid sequence of the variants into a suitable expression vector, transfecting a host cell with the vector, cloning cells that express the desired gene, culturing the obtained stable culture cells, followed by purification.

In addition to amino acid substitution, asparagine-type glycosylation may also be intervened by adding an inhibitor to glycosyltransferase such as tunicamycin to a culture medium of cells (Current Protocols in Protein Science VOL. 2 Chapter 12, John E. Coligan et al. John Wiley & Sons, Inc.).

Furthermore, intervention of asparagine-type glycosylation may also be possible by intervening expression of glycosyltransferase by the use of RNAi, an antisense DNA, and the like.

Besides, the glycosylation may also be intervened by using a glycosyltransferase-deficient cell strain as a host cell.

The FX variant of the present invention may be formulated into a pharmaceutical formulation for use in therapy, diagnosis, and the like. For preparing a formulation for intravenous administration, the composition may usually be dissolved in an aqueous solution containing a physiologically acceptable substance, e.g. sodium chloride, glycine, etc. and having a buffered pH acceptable to physiological conditions. To ensure long-term stability, a lyophilized form of the formulation may also be considered as a final dosage form. Guidelines for a composition for intravenous administration are established by government regulations such as "Minimum Requirements for Biological Products".

Specific use of a pharmaceutical composition comprising the FX variant of the present invention may include the use for the treatment of hemophilia patients with inhibitor where an inhibitor to FVIII or FIX is produced as a consequence of substitution therapy with said FVIII or FIX.

EXAMPLE

The present invention is explained by means of the following Examples but should not be construed to be limited thereto. In Examples, the variants were those expressed in culture supernatant of animal cells (BHK). Reagents for genetic recombination were purchased from TAKARA SHUZO CO., LTD., TOYOBO, Perkin Elmer Applied, and New England Biolabs unless otherwise instructed.

Example 1

Cloning of FX cDNA

A human liver cDNA library (OriGene Technologies) was purchased. Based on a cDNA sequence (shown in SEQ ID NO: 3) encoding an amino acid sequence of FX comprising a prepro sequence as known in literatures (Molecular Basis of Thrombosia and Hemostasis edited by K. A. High and H. R. Roberts, Marcel Dekker, Inc. 1995), PCR was performed using a sense primer for FX synthesis with addition of SalI site (FX-S): GGCGTCGACCCACCATGGATGGGGCGC-CCACTGCACCTC (SEQ ID NO: 10) and an antisense primer with addition of XhoI site (FX-AS): CTCGAGTTAT-CACTTTAATGGAGAGGA (SEQ ID NO: 11) and the PCR products were cloned into a commercially available cloning vector pCRII (Invitrogen). DNA sequencing was conducted as ordinary to confirm the presence of the sequence known in the literatures.

Example 2

Preparation of FX Expression Vector

The expression vector pCAGG (Japanese Patent No. 2824434) was digested with SalI and was ligated thereto the DNA fragment prepared in Example 1 which comprises the sequence encoding FX and has been cleaved with SalI/XhoI.

E. coli JM109 cells were transformed with the resulting vector and cultured on LB agar medium supplemented with ampicillin to select transformed E. coli cells. Colonies as observed were cultured overnight on a commercially available medium and the expression plasmid of interest was extracted and purified to prepare "pCAGFX". DNA sequencing was conducted for the expression vector to confirm the presence of the gene sequence of interest.

Example 3

Introduction of Mutation

The FX cDNA as described in Example 1 was digested with restriction enzymes SalI/XhoI and the fragments were extracted and cloned into pKF vector contained in Site-Directed Mutagenesis kit Mutan-Super Express Km manufactured by TaKaRa. 5'-Phospohrilated synthetic DNA primers (Table 1) were prepared in accordance with the annex of the kit and were used to produce six variants in total with alanine substitution at the charged amino acid of interest. For all the variants, the sequence was confirmed with an automatic DNA sequencer (Beckman Coulter K. K.).

TABLE 1

| Primer | Sequence of primer | SEQ ID NO: |
|---|---|---|
| D63A-S | AAATGTAAAGCCGGCCTCGGG | 12 |
| T159A-S | GACAGCATCGCATGGAAGCCA | 13 |
| T171A-S | CTGGACCCCGCCGAGAACCCC | 14 |
| N181A-S | CTTGACTTCGCCCAGACGCAG | 15 |
| N191A-S | GGCGACAACGCCCTCACCAGG | 16 |
| T443A-S | GAGGTCATAGCGTCCTCTCCA | 17 |

Example 4

Preparation of Variant Expression Vector

The expression vector pCAGG (Japanese Patent No. 2824434) was digested with SalI and was ligated thereto the fragment prepared in Example 3 which comprises the point mutation in the sequence encoding FX and has been cleaved with SalI/XhoI. E. coli JM109 cells were transformed with the resulting vector and cultured on LB agar medium supplemented with ampicillin to select transformed E. coli cells. Colonies as observed were cultured overnight on a commercially available medium and the expression plasmids of interest were extracted and purified.

Example 5

Expression of Variants in Culture Supernatant

With the variant FX expression vectors obtained in Example 4, gene transfection was performed to BHK cells using a commercially available lipofectin reagent (TransIT; TaKaRa) and transient expression culture supernatant was collected on Day 3 after the transfection. The supernatant was concentrated 10-fold with Centricon YM-10 (Millipore) and the expression level was quantified with a commercially available ELISA kit (Funakoshi Co., Ltd.) for FX quantification (Table 2).

Example 6

Measurement of Coagulation Activity of Variants

A coagulation activity of the variants was measured as ordinary by a coagulation approach using FX deficient plasma. Each of the purified variants were diluted to 10 ng/ml to 10 µg/ml with a Veronal buffer (28.5 mM sodium barbital, 125.6 mM NaCl, pH 7.35), mixed with FX deficient plasma, and after incubation at 37° C., added with an APTT reagent and then with 0.025 M calcium chloride solution to initiate a coagulation reaction. A coagulation time was measured and a coagulation activity was calculated from a standard curve and a dilution rate (Table 2). In addition, the coagulation activity was converted into the activity per protein level (Example 5; measured by ELISA) to give a specific activity (Table 2). As a result, among the FX variants of the present invention were those variants (N181A, N191A) that showed a higher expression level and a higher coagulation activity than those of FX from plasma or a wild-type recombinant FX (Table 2).

TABLE 2

| Variant | Expression level*2 | Coagulation activity (ng/mL) | Specific activity*3 | Ratio to FX from plasma*4 |
|---|---|---|---|---|
| A*1 | — | — | 1 | 1 (3.0) |
| B*1 | 568 | 189 | 0.33 | 0.33 (1) |
| C*1 | 361 | 49 | 0.14 | 0.14 (0.42) |
| D*1 | 504 | 302 | 0.60 | 0.60 (1.82) |
| E*1 | 568 | 29 | 0.05 | 0.05 (0.15) |
| F*1 | 959 | 517 | 0.54 | 0.54 (1.64) |
| G*1 | 1036 | 2554 | 2.47 | 2.47 (7.48) |
| H*1 | 547 | 358 | 0.65 | 0.65 (1.97) |

*1A: Standard FX from plasma; B: Wild-type recombinant FX; C: D63A variant (SEQ ID NO: 4); D: T159A variant (SEQ ID NO: 5); E: T171A variant (SEQ ID NO: 6); F: N181A variant (SEQ ID NO: 7); G: N191A variant (SEQ ID NO: 8); H: T443A variant (SEQ ID NO: 9)
*2ELISA (ng/mL)
*3Coagulation activity/ELISA
*4(Ratio to wild-type recombinant)

Example 7

Western Blot of Recombinant FXs

The enzymes of the present invention were detected by Western blot using ordinary procedures (Current Protocols in Molecular Biology: Chapter 10 analysis of proteins, Chapter 11 immunology, and the like). Specifically, the expression of the recombinant FXs was confirmed by SDS-PAGE under reduced conditions of culture supernatant of BHK cells expressing the variant obtained in Example 5, and after transfer to PVDF membrane, reaction with an anti-human FX monoclonal antibody (FIG. 1). As a result, it was apparent that the variants with mutations at the asparagine-type glycosylation site, Asn181 and Asn191, were predominantly expressed as a two-chain protein.

The invention claimed is:

1. A recombinant Factor X with inhibited glycosylation, wherein the recombinant Factor X is obtained by a process comprising inhibiting glycosylation by substituting alanine for asparagine at position 181 (N181A) of SEQ ID NO: 1.

2. A composition comprising:
   the recombinant Factor X according to claim 1; and
   a physiologically acceptable excipient.

3. A method of treating hemophilia, wherein the method comprises administering to a subject in need thereof an effective amount of the composition according to claim 2.

4. A recombinant Factor X with inhibited glycosylation, wherein the recombinant Factor X is obtained by a process comprising inhibiting glycosylation by substituting alanine for asparagine at position 181 (N181A) and position 191 (N191A) of SEQ ID NO: 1.

5. A composition comprising:
   the recombinant Factor X according to claim 4; and
   a physiologically acceptable excipient.

6. A method of treating hemophilia, wherein the method comprises administering to a subject in need thereof an effective amount of the composition according to claim 5.

7. A recombinant Factor X with inhibited glycosylation, wherein the recombinant Factor X is obtained by a process comprising inhibiting glycosylation by substituting alanine for threonine at position 159 (T159A) of SEQ ID NO: 1.

8. A composition comprising:
   the recombinant Factor X according to claim 7; and
   a physiologically acceptable excipient.

9. A method of treating hemophilia, wherein the method comprises administering to a subject in need thereof an effective amount of the composition according to claim 8.

10. A recombinant Factor X with inhibited glycosylation, wherein the recombinant Factor X is obtained by a process comprising inhibiting glycosylation by substituting alanine for threonine at position 443 (T443A) of SEQ ID NO: 1.

11. A composition comprising:
    the recombinant Factor X according to claim 10; and
    a physiologically acceptable excipient.

12. A method of treating hemophilia, wherein the method comprises administering to a subject in need thereof an effective amount of the composition according to claim 11.

13. A recombinant Factor X with inhibited glycosylation, wherein the recombinant Factor X is obtained by a process comprising inhibiting glycosylation by substituting alanine for threonine at position 159 (T159A) and position 443 (T443A) of SEQ ID NO: 1.

14. A composition comprising:
the recombinant Factor X according to claim 13; and
a physiologically acceptable excipient.

15. A method of treating hemophilia, wherein the method comprises administering to a subject in need thereof an effective amount of the composition according to claim 14.

16. A recombinant Factor X with inhibited glycosylation, wherein the recombinant Factor X is obtained by a process comprising inhibiting glycosylation by substituting alanine for asparagine at position 181 (N181A) and position 191 (N191A) of SEQ ID NO: 1, and substituting alanine for threonine at position 159 (T159A) and position 443 (T443A) of SEQ ID NO: 1.

17. A composition comprising:
the recombinant Factor X according to claim 16; and
a physiologically acceptable excipient.

18. A method of treating hemophilia, wherein the method comprises administering to a subject in need thereof an effective amount of the composition according to claim 17.

* * * * *